United States Patent [19]

Filhol

[11] Patent Number: 5,263,996
[45] Date of Patent: Nov. 23, 1993

[54] DENTAL PIN

[76] Inventor: Stuart J. Filhol, Cuilin Cottage, Desertserbes, Enniskeane, Co. Cork, Ireland

[21] Appl. No.: 779,032

[22] Filed: Oct. 18, 1991

[30] Foreign Application Priority Data

Oct. 18, 1990 [GB] United Kingdom ............... 9022709

[51] Int. Cl.⁵ .................................................. A61C 5/08
[52] U.S. Cl. ...................................... 433/221; 433/220
[58] Field of Search ............... 433/219, 220, 221, 224, 433/225

[56] References Cited

U.S. PATENT DOCUMENTS

| | | | |
|---|---|---|---|
| 2,655,724 | 10/1953 | Brooks | 433/221 |
| 2,705,837 | 4/1955 | Gerlach | 433/221 |
| 3,590,486 | 7/1971 | Brenner | 433/225 |
| 3,919,774 | 11/1975 | Fishman | 433/224 |
| 4,449,937 | 5/1984 | Weissman | 433/225 |
| 4,490,116 | 12/1984 | Deutsch et al. | 433/225 X |
| 4,515,565 | 5/1985 | Winter-Moore et al. | 433/221 |
| 4,600,391 | 7/1986 | Jacob | 433/221 X |
| 4,728,292 | 3/1988 | Lustig et al. | 433/225 |
| 4,778,388 | 10/1988 | Yuda et al. | 433/221 |
| 4,917,606 | 4/1990 | Miller | 433/225 |

FOREIGN PATENT DOCUMENTS

| | | | |
|---|---|---|---|
| 606163 | 11/1934 | Fed. Rep. of Germany | 433/220 |
| 833837 | 3/1952 | Fed. Rep. of Germany | 433/220 |

Primary Examiner—Gene Mancene
Assistant Examiner—Nicholas D. Lucchesi
Attorney, Agent, or Firm—Ostrolenk, Faber, Gerb & Soffen

[57] ABSTRACT

A retentive dental pin comprising in sequence a lower portion which can be secured within the dentine of a tooth, and a head portion to which a tooth restoration may be secured, a detachable connection, and a fixing portion attached to the head portion by the detachable connection, characterised in that the head portion is connected to the lower portion by dentine-engaging structure comprising an inwardly and downwardly extending surface carrying grooves shaped to screw into the dentine.

13 Claims, 2 Drawing Sheets

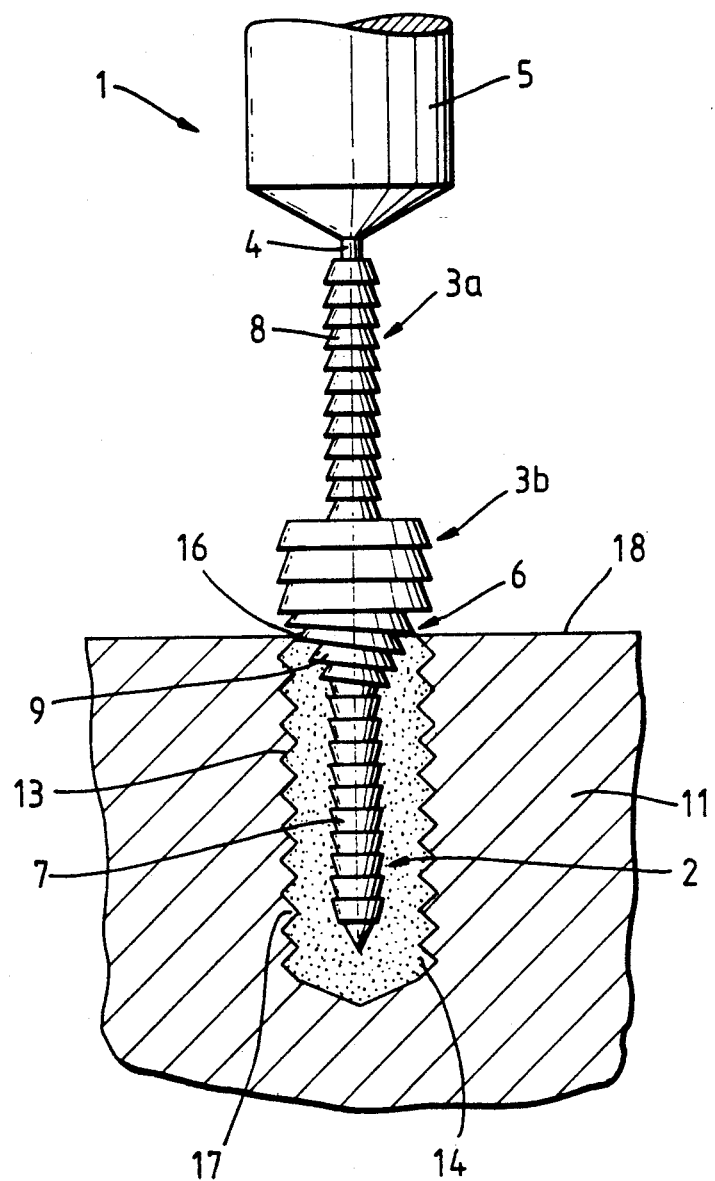

DENTAL PIN

This invention relates to an improved retentive dental pin and to its use in securing tooth restorations, for example fillings, crowns, enamel films to the dentine of an existing tooth. The dental pin according to the present invention can also be used to further secure crowns held by dental posts fitted into the root canal, by preventing rotation of these pots.

Various ways of fixing dental posts and pins are known, usually they involve screwing. A particular post fixing method is disclosed in E-P-A-0370676 and the prior art referred to in that application.

In general a retentive dental pin has an upper portion to which a tooth restoration can be secured, and a lower portion that extends downwards from the upper portion and can be secured within the dentine of the tooth. The pins are fitted by first drilling a hole of sufficient depth and diameter to receive the lower portion of the pin; the pin is then fitted and secured within the hole, and the particular tooth restoration secured to the upper portion of the pin.

Known dental pins include the threaded pin, which can be threaded into a pre-tapped hole, or can itself be used as a self-tapping screw and self-threaded into a slightly undersized pilot hole; the cemented pin; and the friction-lock pin.

Particular examples of prior art in this field include GB 1588235 when discloses a self-tapping pin attached to a driver; the pin is screwed into a pre-drilled undersized hole and the driver is then unthreaded from the pin with the aid of a lubricant. Another example of a dental pin is sold under the trade name Filpin Nova and is a threaded pin having a fixer portion for attachment to the driver connected to the pin head via a low shear connection, or break-off point. The Filpin Nova is screwed into a pre-drilled, under sized hole until the torque on the shank is such that it causes shearing at the break-off point, so exposing the head of the pin to which the restoration can then be attached. Unfortunately this screw-in method stresses the dentine because of the need to develop sufficient torque to shear the break-off point.

The height of the pin above the surface of the existing dentine is an important factor as regards retention of the restoration. With prior art pins this is dictated by both the diameter and the depth of the hole into which the pin is to be fitted. In pins having shearable connections e.g. Filpin Nova, it is primarily the accuracy of drilling of the diameter which is important, since too small a diameter will result in early shearing, and too large a diameter in late shearing, or no shearing at all. It is therefore necessary to drill to exactly the correct dimensions for the particular pin to be used as otherwise too much or too little of the head of the pin is exposed and the pin will be ineffective. A large number of differently sized pins are available to minimise these difficulties.

In addition, variations in the hardness of the dentine from patient to patient has necessitated the provision of pus of difference shear points; hard dentine causes early shearing, and soft dentine causes late or no shearing.

It would therefore be desirable to provide a dental retention pin which is independent of the accuracy to which the dimensions of the hole into which it is to be fitted is drilled; independent of the patient (rehardness of dentine) in which it is to be used; and also to provide a pin which exerts minimum stress on the surrounding dentine when fitted.

In the following specification the words "upper" and "upwardly" are used to indicate the direction towards the tooth restoration and "downward" and "downwardly" to mean the converse.

According to a first aspect of the present invention a dental retention pin is provided comprising in sequence a lower portion which can be secured within the dentine of the tooth, and a head portion to which a tooth restoration may be secured, a detachable connection, and a fixing portion attached to the head portion by the detachable connection, characterised in that the head portion is connected to the lower portion by a dentine-engaging portion comprising an inwardly and downwardly extending surface carrying grooves shaped to screw into the dentine.

According to a second aspect of the present invention a method is provided for securing a tooth restoration using a retentive dental pin as defined in the first aspect of the present invention comprising drilling a pin-receiving hole in the dentine, securing the lower portion of the pin inside the hole, and securing the tooth restoration to the upper portion of the pin characterised in that the transverse dimensions of the said hole are larger than those of the lower portion of the pin but smaller than those of at least part of the dentine-engaging means of the pin, curable cement is introduced into the hole, the lower portion of the pin is pushed into the hole and defines an annulus between the pin and the wall of the hole, the curable dement is displaced outwards into the annulus, the dentine-engaging means of the pin inter-engages with the dentine at the mouth of the hole and suspends the pin in the hole, the fixing portion is twisted to screw the grooves in the inwardly extending shoulder into the dentine at the mouth of the hole and to detach the pin at the detachable connection, the cement is cured and a tooth restoration is secured to the head portion of the pin.

Pushing the dental pin into the hole rather than screwing it in reduces the stress on the dentine surrounding the pin, thereby reducing resultant damage, e.g. cracking, of the dentine. The dentine-engaging means of the pin, as mentioned above, inter-engages with the dentine at the mouth of the pre-drilled hole into which the pin is to fit. The dentine-engaging means effectively acts as a depth control, arresting the pin at the desired height in the hole independent of inaccuracies common in hole drilling. The dentine-engaging portion also gives the pin the added advantage over prior art pins that it suspends the pin substantially motionless in the hole while the cement is cured, effecting much firmer bonding of the lower portion pin within the dentine of the tooth.

The grooves in the dentine-engaging means can be of any shape that will result in it tending to bite into the dentine at the mouth of the drilled hole. Preferably they are in the form of a helix, although part-helical grooves can be adequate.

The fixing portion of the dental pin, sometimes known as the shank, acts to attach the pin to the drill head, and facilitates the fitting of the pin into the dentine which has proved difficult in the past due simply to the size and shape of such pins. In addition, it also acts as a lever to transmit torque to the detachable connection when the pin has reached its required position in the dentine and the grooves of the dentine-engaging means begin screwing into the dentine, so detaching the pin from the drill. The fixing portion may be monolithic with the rest of the pin, or alternatively it may be a separate portion detachably attached to the head of the pin by, for example, a glue. The fixing portion therefore may be made of the same or different material to the rest of the pin. Attachment of the fixing portion to the drill is generally by a sleeve portion locked into the drill itself, which is usually made of a plastic material.

The lower portion, for securing into the dentine of the tooth, may be cylindrical in shape or may be tapered in a direction away from the head portion. The lower portion usually has a rough surface to enhance its bonding within the dentine. The surface may be in the form of a sand-blasted surface, but preferably comprises transverse notches distributed along some, but usually all, of the length of the lower portion of the pin. The notches preferably open in an upwardly and outwardly direction in order that they tend to resist an upward pull once implanted within the dentine.

The notches can be a series of discrete notches, but are preferably a plurality of substantially parallel notches, with each notch extending substantially around the lower portion of the dental pin. The plurality of substantially parallel notches can be provided by one or more helical grooves extending around the lower portion, but generally are provided by a series of independent grooves.

The size and number of the notches in the surface of the lower portion of the pin will effect the ultimate bonding strength of the pin within the dentine. However, the provision of the notches must not result in an unacceptable reduction in the strength of the pin. A small number of deep notches risks weakening the pin and so preferably there are a large number of small notches.

In the tapered embodiment, the pitch of the grooves (i.e. the actual spacing between the bases of adjacent grooves) towards the tip of the lower portion of the pin will tend to be less than that towards the upper end, again being dependent upon the strength characteristics of the pin.

Irrespective of if the pin is cylindrical or tapered, the pitch of the grooves is generally less than 0.2 mm, and usually below 0.05 mm. It must not be too small, as otherwise the bonding agent used to secure the pin in the dentine may not be able to migrate into the recesses of the grooves. The depth of each groove should always fall within the range described above for the pitch, and usually the depth of each groove is quarter to one times the pitch.

The head portion of the dental pin may also be modified to aid securement of the restoration to it. This can be done by sand-blasting, but this is rather a difficult process. Therefore, the pin head preferably also comprises a grooved structure. A preferred arrangement is with the grooves opening in a downward and outward direction, so acting against any forces which will tend to pull the tooth restoration off the pin and away from the tooth.

In one embodiment of the invention the head portion of the pin has a larger transverse dimension than the lower portion. In which case the transverse dimension of the head portion of the pin are in the range 0.8 mm to 1.2 mm and those of the lower portion are in the range 0.5 mm to 1.0 mm, in the case of a cylindrical lower portion. Substantially the same dimensions comprise the average dimensions of a pin having a tapered lower portion, gradually decreasing in dimensions to the end furthermost from the head portion.

In this particular embodiment the lower portion end that abuts the dentine-engaging means has smaller transverse dimensions than the head of the pin. In general, the difference in the transverse dimensions of the lower portion where it abuts the dentine-engaging portion and the head portion (at its largest part) is approximately in the range 0.15 to 0.5 mm.

The pitch of the grooves in the head portion in this embodiment is generally larger than that in the lower portion, and is generally in the range of 0.05–0.2 mm, and is typically around 0.1 mm.

A second embodiment of the pin according to the invention has a head portion which comprises a narrow, elongated portion and an outwardly extending portion which connects the elongated portion to the dentine-engaging means. The outwardly extending portion comprises a generally upward facing surface. In this context, a generally upwardly facing surface means a surface which is substantially horizontal, or which is inclined downwardly at an angle to the horizontal. The outwardly extending portion may carry grooves in its surface which preferably extend downwards and outwards, as is preferred for the grooves in the remainder of the head portion.

In this embodiment the transverse dimension of the narrow, elongated portion and the end of the lower portion which abuts the dentine-engaging means will be substantially the same, and will be in the range 0.6 to 0.8 mm.

The head portion is releasably attached to the fixing portion through a detachable connection, or break-off point. Typical values of the strength of this detachable connection are generally below 100 gram centimeters and are usually in the order of 20 gram centimeters. (In fact the strength of this connection need only be sufficiently strong to attach the pin to the fixing portion). This is much less than the force required for normal dental pins which have shear-points of strengths typically between 100 to 200 gram centimeters. The stress exerted on the dentine is dependent on the strength of the shear-point, therefore reducing this strength has the advantageous effect of reducing the stress on the dentine. In addition, the shoulder arrangement aids in making the shear strength effectively independent of the hardness of the dentine.

The detachable connection may be a shearable connection or any other temporary connection caused by, for example, weakly gluing the head portion to the fixing portion.

It is preferred that the surface area of the lower portion is approximately equal to the combined surface area of the dentine-engaging means and head portion for reasons of establishing the best force equilibrium when the pin is secured and the restoration attached.

The particular pin to be used depends upon the particular restoration to be fixed to the tooth. For restorations having a large surface area a plurality of pins may be used depending on, thickness of the restoration to be applied. For fixing a very thin enamel film to the dentine it is necessary that the pin has a very shallow head portion with a relatively large surface e.g. a pin according to the first embodiment, generally having a length (as measured from the surface of the head portion to the end of the lower portion furthermost from the head portion), in the order of around 2.0 mm, of which the lower portion comprises around 1.3 mm and the dentine-engaging means and head portion together comprise the remainder i.e. around 0.7 mm. Whereas for thicker restorations an extended head portion may be required e.g. a pin according to the second embodiment, in which case the length of the pins may be about 4 mm, about 2 mm each extending above and below the dentine. In the light of the many different types of restoration the dimensions of any particular pin will vary somewhat.

The materials from which the dental pin can be made are generally selected from inert materials already proven to be of use in medical applications, and completely resistant to attack from bodily fluids; suitable materials include a special stainless steel used extensively in bone and body transplants which has excellent resistant to corrosion, known as 316-Grade stainless steel, pure titanium and gold; titanium is preferred.

The cement used to secure the lower portion of the pin with the dentine comprises conventional bonding agents, and includes zinc phosphate cements, glass ionomer cements and epoxy cements, and any other cement commonly used in bonding dental pins, posts etc. into a patient's tooth.

Preferably the hole is provided with projections in the dentine making up the walls of the hole. As a result, the bonding agent used is trapped between the notches on the lower portion of the pin and these projections in the dentine. Preferably the projections in the dentine extend downwardly and inwardly, i.e. in an opposite direction to the lower portions notches which preferably extend upwardly and outwardly, this leads to better bonding of the pin within the dentine. Therefore, the securement of the pin in the hole depends largely on the shear strength of the bonding agent rather than the adhesive strength of the bonding agent to the pin and the hole wall.

The described projections in the walls of the pre-drilled hole using a reamer that is much smaller than, but is otherwise similar to the type described in the afore-mentioned E-P-A-0370676. The reamer must have a slightly larger diameter than that of the pre-drilled hole, so that it bites into the dentine on all sides of the hole and forms projections in the dentine. The diameter of the reamer is generally in the range 0.5 to 1.1 mm. The type of projections formed in the walls of the hole should relate to those in the lower portion of the pin to be most favourable for bonding of the pin into the dentine.

The pin-receiving hole is drilled to have a diameter larger than the transverse dimensions that of the lower portion of the pin, yet smaller than at least part of the shoulder of the pin. The curable cement is inserted into the hole prior to insertion of the pin. The pin is pushed into the hole until part of the dentine-engaging means comes into contact with the rim of the hole and bites into the dentine at that place, preventing any further downward movement of the pin. Due to the difference in the dimensions of the hole and the pin's lower portion an annulus is defined between the walls of the hole and the lower portion, into which the cement is forced on insertion of the pin.

The pin is released from its fixing element by detaching at the break-off point arranged between the head portion and the fixing portion. This detachment action is reliant on the fact that the shoulder portion of the pin arrests the pin within the hole by a self-trapping mechanism; rotation of the fixing element relative to the trapped pin causes detachment at the break-off point just above the head portion, leaving the head portion free to accept the particular tooth restoration to be applied.

Curing of the cement is preferably after detaching at the break-off points, primarily for reasons of patient comfort. However, curing can take place before detachment, preferably with the use of a fast-curing cement.

Curing the cement while the dentine-engaging means holds the pin suspended in the pre-drilled hole which prevents any destructive movement of the pin in the hole; which could lead to insecure bonding of the pin in the dentine; this has been a problem common to prior art pins.

Attachment of the tooth restoration is preferably after curing of the cement, since the pin will be more securely fixed within the dentine. However, the restoration may if desired, be attached before curing.

The invention is further illustrated in the accompanying drawings:

FIG. 3 is a side view of a dental pin according to a second embodiment of the present invention with lower portion pushed into the dentine.

Figure 1:
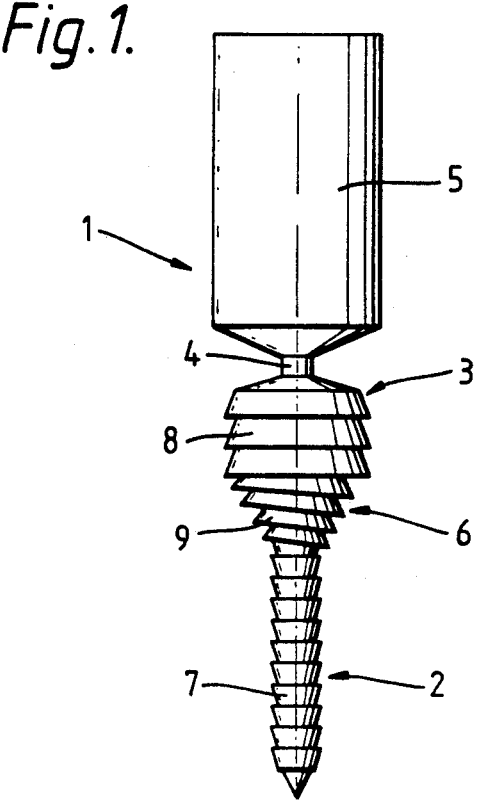
FIG. 1 is a side view of a dental pin according to a first embodiment the present invention.

Referring to FIG. 1, the dental retention pin (1) comprises a lower portion (2) which can be secured within the dentine of the tooth, and a head portion (3) to which a tooth restoration may be fixed.

FIG. 1 shows a preferred embodiment of the dental retention pin (1) according to the present invention wherein the lower portion (2) has a plurality of grooves (7) in its surface extending substantially along its entire length; the grooves (7) open upwardly and outwardly. The head portion (3), to which a tooth restoration may be fixed, also has a plurality of grooves (8) in its surface, these open in a downwards and outwards direction. The head portion of the pin has a larger transverse dimension than the lower portion of the pin and is connected to that lower portion by a through dentine-engaging means (6) which comprises an inwardly and downwardly extending surface carrying grooves, shown as helical grooves, to screw into the dentine. A shearable connection (4) attaches the head portion of the pin to a fixing portion (5), which in turn is used to attach the pin to a drill head (not shown) which is used to insert the pin into the tooth.

Figure 2:
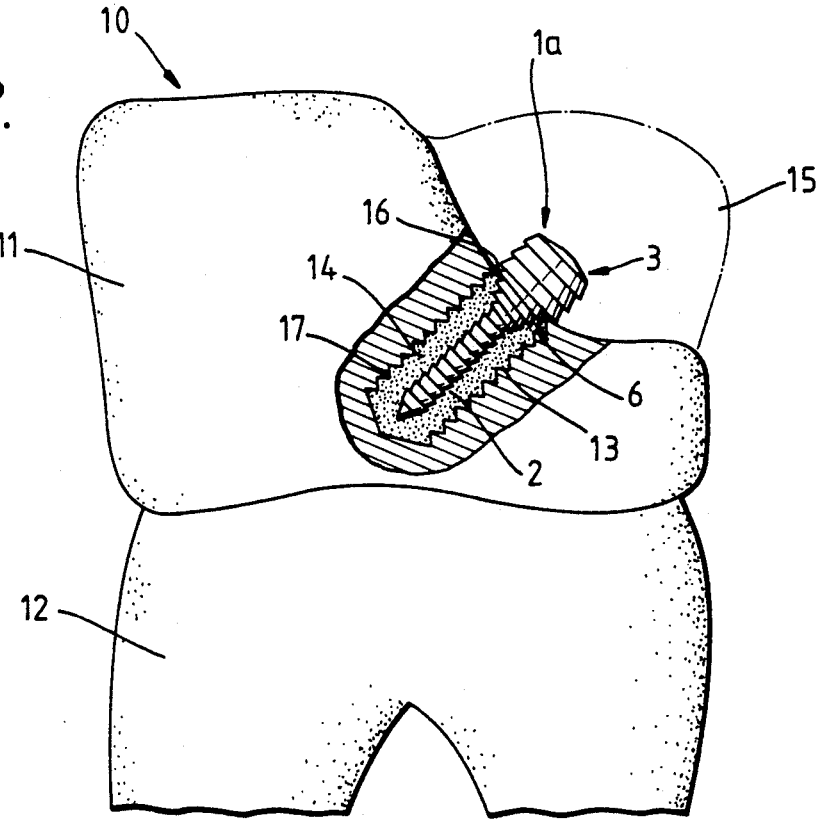
FIG. 2 is a diagrammatic cross-section through a tooth to which a restoration has been fixed using a dental pin according to the present invention.

Referring to FIG. 2, a tooth (10) comprising dentine (11) and root portion (12) is fitted with a tooth restoration (15) using a dental retentive pin (1a) which has been released from its fixing portion at the shearable connection, exposing the head portion (3) to which the restoration is then fitted.

The lower portion (2) of the pin is bonded within a pre-drilled hole (13), having projections (17) in the side walls, in the dentine (11). Bonding is accomplished by curing the curable cement which has been displaced into an annulus (14), defined between the lower portion (2) of the pin and the walls of the hole (13), on insertion of the pin into the hole. The dentine-engaging means (6) of the pin bites into the dentine at the mouth (16) of the hole, arrests the pin in that position and so serves to shear the pin from its fixing portion when sufficient torque is applied to the shearable connection (see FIG. 1). The dentine-engaging means holds the pin stationary while the bonding cement cures.

Referring to FIG. 3, the pin (1) has a head portion comprising narrow, elongated portion (3a) and an outwardly extending portion (3b) which connects the elongated portion to the dentine-engaging means (6). The dentine-engaging means in turn connect the head portion to the lower portion (2). The same reference numbers used in FIG. 1 indicate the remaining parts of the pin; the same reference numbers as in FIG. 2 are used to indicate the parts of the tooth, except the surface of the dentine (18).

I claim:

1. A retentive dental pin comprising in sequence
    a lower portion which can be secured within the dentine of a tooth, and
    a head portion to which a tooth restoration may be secured,
    a detachable connection, and
    a fixing portion attached to the head portion by the detachable connection, wherein
    the head portion is connected to the lower portion by dentine-engaging means comprising in inwardly and downwardly extending tapered surface carrying helical grooves shaped to screw into the dentine and
    the lower portion has a surface which comprises transverse notches distributed along at least part of its length and the notches open in an upwardly and outwardly direction.

2. A dental pin according to claim 1 wherein the notches are in the form of a plurality of substantially parallel notches selected from at least one helical groove and a series of independent grooves.

3. A dental pin according to claim 1 wherein the pitch of the notches in the lower portion is less than 0.2 mm.

4. A dental pin according to claim 1 wherein the lower portion is tapered in a direction away from the head portion.

5. A dental pin according to claim 1 wherein the head portion comprises a grooved structure having grooves opening in a downward and outward direction.

6. A dental pin according to claim 1 wherein the head portion has a larger transverse dimension than the lower portion, the transverse dimension of the head portion being from 0.8 mm to 1.2 mm and the transverse dimension of the lower portion being from 0.5 mm to 1.0 mm, and the difference between the transverse dimensions of the head portion and the transverse dimension of the lower portion where it joins the dentine-engaging means is in the range of 0.15 to 0.5 mm.

7. A dental pin according to claim 6 wherein both the head and lower portions have notches structures, and the pitch of notches in the head portion is larger than that in the lower portion, and is in the range of 0.05–0.2 mm.

8. A dental pin according to claim 1 wherein the detachable connection has a strength of below 100 gram centimeters.

9. A dental pin according to claim 8, wherein the detachable connection has a strength below 20 gram centimeters.

10. A dental pin according to claim 1 wherein the surface area of the lower portion is approximately equal to the combined surface area of the dentine-engaging means and head portion.

11. A dental pin according to claim 1, wherein the pitch of the grooves in the lower portion is less than 0.05 mm.

12. A retentive dental pin comprising in sequence
    a lower portion which can be secured within the dentine of a tooth, and
    a head portion to which a tooth restoration may be secured,
    a detachable connection, and
    a fixing portion attached to the head portion by the detachable connection, wherein
    the head portion is connected to the lower portion by dentine-engaging means comprising an inwardly and downwardly extending tapered surface carrying helical grooves shaped to screw into the dentine and
    the head portion comprises a narrow elongated portion and an outwardly extending portion which connects the elongated portion to the dentine-engaging means.

13. A method of securing a tooth restoration using a retentive dental pin which comprises the steps of
    providing a retentive dental pin comprising in sequence a lower portion which can be secured within the dentine of a tooth, a head portion to which a tooth restoration may be secured, a detachable connection, and a fixing portion attached to the head portion by the detachable connection, wherein the head portion is connected to the lower portion by dentine-engaging means comprising an inwardly and downwardly extending tapered surface carrying helical grooves shaped to screw into the dentine,
    drilling a pin receiving hole in the dentine such that the transverse dimensions of the hole are larger than those of the lower portion of the pin but smaller than those of at least the dentine engaging means of the pin,
    introducing a curable cement into the hole,
    pushing the lower portion of the pin into the hole so as to define an annulus between the pin and the wall of the hole and displacing the curable cement outwardly into the annulus,
    inter-engaging the dentine engaging means of the pin with the dentine at the mouth of the hole thereby suspending the pin in the hole,
    twisting the fixing portion of the pin to screw the grooves of the inwardly and downwardly extending tapered surface of the dentine engaging means into the dentine at the mouth of the hole and to detach the pin at the detachable connection,
    curing the cement and
    securing a tooth restoration to the upper portion of the pin.

* * * * *